United States Patent [19]

Manning

[11] Patent Number: 5,427,563
[45] Date of Patent: Jun. 27, 1995

[54] BREAST WRAP

[76] Inventor: Judith W. Manning, P.O. Box 5144, Winter Park, Fla. 32793

[21] Appl. No.: 46,775

[22] Filed: Apr. 13, 1993

[51] Int. Cl.⁶ ............................................. A41C 3/00
[52] U.S. Cl. .................................. 450/79; 450/23; 450/57; 450/85; 450/72; 2/73
[58] Field of Search .................. 450/1, 23, 31, 32, 57, 450/60, 79, 80, 82, 83, 84, 85, 89, 72; 2/59, 24, 160, 162, 170, 247; 128/379, 384, 385, 402, 403; 602/14, 75, 60, 61

[56] References Cited

U.S. PATENT DOCUMENTS

| | | | |
|---|---|---|---|
| 268,574 | 12/1882 | Thurlow | 2/247 |
| 647,155 | 4/1900 | Lush | 450/155 |
| 1,019,537 | 3/1912 | Schwenkler | |
| 1,532,250 | 4/1925 | Lindemann | 450/83 |
| 1,648,464 | 11/1927 | Rosenthal | |
| 2,662,522 | 12/1953 | Muller | 128/155 |
| 2,723,396 | 11/1955 | Stack | 2/42 |
| 3,054,400 | 9/1962 | Lizio | 602/60 |
| 3,189,028 | 6/1965 | Dormire | 128/155 |
| 3,529,601 | 9/1970 | Kirkland | 602/60 |
| 4,218,781 | 8/1980 | Lieberman | 2/247 |
| 4,527,566 | 7/1985 | Abare | 128/403 |
| 4,676,247 | 6/1987 | Van Cleve | 128/403 |
| 4,688,572 | 8/1987 | Hubbard et al. | 128/402 |
| 5,060,648 | 10/1991 | Zarkesh | 128/402 |

OTHER PUBLICATIONS

1940 Sears Catalog Entry on Women's Knit Cotton Binders.
1948 Sears Catalog Entry on Knit Maternity Binders.

*Primary Examiner*—Jeanette E. Chapman
*Attorney, Agent, or Firm*—Allen, Dyer, Doppelt, Franjola & Milbrath

[57] ABSTRACT

A breast wrap (10) has two rectangular non-stretching panels (11, 12) of cotton flannel material joined over a user's back by short elastic strips (16, 17), and joined in overlapping relationship across the breasts by upper and lower complementary hook-and-loop fasteners (28, 29, 30, 31) running marginally along upper and lower longitudinal edges (24, 25, 26, 27). The panels run lengthwise in opposite directions from the user's back, under one arm, across both breasts, and terminate at a point located under the other arm; the panels run widthwise from above the breasts to below the breasts; and the fasteners are located so they will not be pressed into the breasts. Two rectangular open-ended pouches (40, 41) having pockets (40) for crushed ice, are held between the overlapping panels by additional hook-and-loop fasteners (47, 48) that mate with fasteners (28, 29, 30, 31).

3 Claims, 2 Drawing Sheets

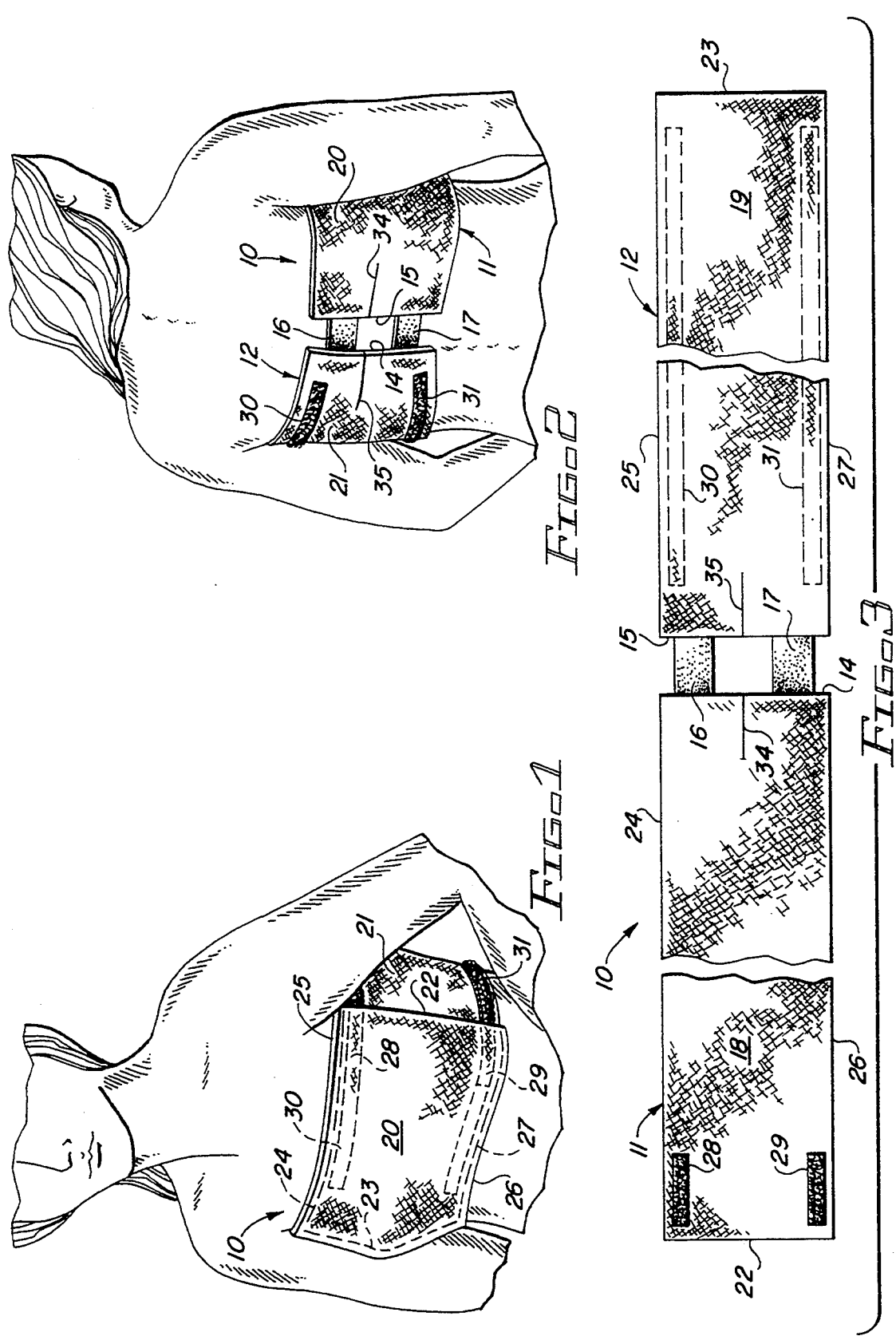

BREAST WRAP

BREAST WRAP

The present invention relates to a device for compressing the breasts against the chest wall to alleviate discomfort associated with post-partum engorgement in non-nursing mothers, and the like.

BACKGROUND OF THE INVENTION

The breasts or mammae are accessory glands of the generative system. Gray's Anatomy defines the female breasts as "two large hemispherical eminences situated toward the lateral aspect of the pectoral region, corresponding to the intervals between the third and sixth or seventh ribs, and extending from the side of the sternum to the axilla." The breasts increase in size during pregnancy and become engorged with milk following delivery.

To reduce the pain and leakage associated with engorgement, non-nursing women traditionally turn to elastic bandages, tight bras or old-fashioned wraps as alternatives to milk drying drugs which entail risks of undesirable side effects. Nursing mothers, too, turn to such devices, both for added supporting during jogging or other exercise, and to alleviate engorgement during the transition period at conclusion of breast-feeding.

Elastic breast binders or tight bras can cut into the breasts, causing damage or clogging breast ducts, which can lead to painful mastitis. Also, such devices apply pressure unevenly to breast tissue and can be so tight as to constrict circulation or breathing. Conventional non-elastic binders, comprising continuous plain strips of, e.g., 9"×44" medium weight cotton flannel are more comfortable, but provide no ready means of fastening, so can be self-applied only with much difficulty. The degree of maneuverability necessary to encircle the body with the binder and properly apply safety pins actually stimulates lactation, so contributes to the engorgement problem.

U.S. Pat. No. 5,060,648 discloses a breast binder comprising left, right and central trapezoidal panels, wherein the left and right panels are brought into overlapping relationship over the breasts and held in place by VELCRO TM hook-and-loop closure elements. To hold ice bags between the overlapping panels, complementary VELCRO TM fasteners are positioned at both sides of the overlapping panels. The top side of each overlapping panel is made convex. The described binder has several disadvantages. In order to achieve the desired compression, the binder must be tightly wrapped. However, this interferes with non-constricted breathing which requires allowance for chest expansion and contraction. The positioning of the fasteners centrally of the binder width places them awkwardly in positions to be pressed against the chest wall, and interferes with placement of ice bags in the axilla regions. Furthermore, no mechanism is provided beyond the tightness of the wrap to hold the bags in place. Maintenance of the shape of the panel convex sides, moreover, requires starching or stiff material, which interferes with wearer comfort.

SUMMARY OF THE INVENTION

The present invention provides a simple wrap for comfortably and evenly immobilizing breasts and compressing them against the chest wall, without constricting circulation or breathing, and providing convenient out-of-the-way fastening means so the wrap can be self-applied with minimum wearer movement.

In accordance with a preferred embodiment, described in greater detail below, a breast wrap comprises two rectangular non-stretching panels of cotton flannel material joined over the hollow of a wearer's back by short, upper and lower heavy elastic strips, and joined in overlapping relationship across the breasts by upper and lower complementary hook-and-loop fasteners running horizontally, marginally along upper and lower longitudinal edges. Two rectangular open-ended pouches are provided, having like fasteners for attachment to corresponding elements of the overlapping panels.

BRIEF DESCRIPTION OF THE DRAWINGS

Embodiments of the invention have been chosen for purposes of illustration and description and are shown in the accompanying drawings, wherein:

FIG. 1 is a front perspective view of a breast wrap in accordance with the invention, shown applied over the breasts of a wearer;

FIG. 2 is a rear perspective view of the same wrap, applied as in FIG. 1;

FIG. 3 is a front elevation view of the unfurled wrap of FIGS. 1 and 2;

Throughout the drawings, like elements are referred to by like numerals.

DETAILED DESCRIPTION OF PREFERRED EMBODIMENTS

Figure 4:
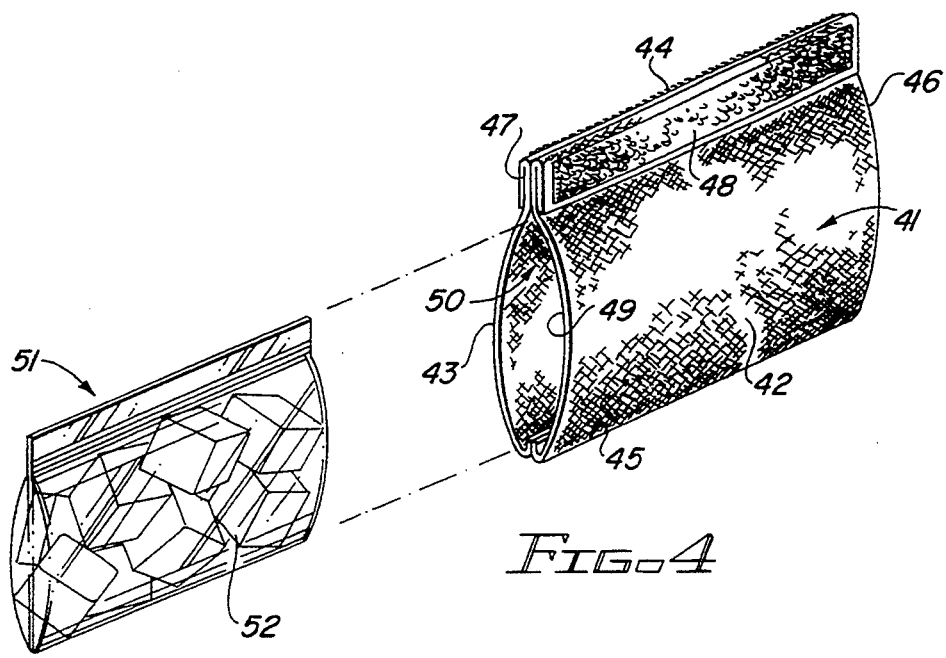
FIG. 4 is a perspective view of an ice bag pouch usable with the wrap of FIGS. 1-3.

As shown in FIGS. 1-3, an exemplary implementation of a breast wrap 10 in accordance with the invention comprises first and second horizontally longitudinally extending elongated panels 11, 12 of non-stretchable cotton flannel material, joined at proximal longitudinally-spaced lateral edges 14, 15 by upper and lower elongated strips 16, 17 of longitudinally extending heavy elastic material. The panels 11, 12 have respective inner 18, 19 and outer 20, 21 rectangular faces joined peripherally at seams running along proximal 14, 15 and distal 22, 23 lateral edges and upper 24, 25 and lower 26, 27 longitudinal edges. Panel 11 includes upper and lower VELCRO TM hook fastener elements 28, 29 extending longitudinally marginally respectively adjacent edges 24, 26 on face 18, for a short distance from a point adjacent the edge 22. Panel 12 includes upper and lower complementary VELCRO TM loop fastener elements 30, 31 extending longitudinally marginally respectively adjacent edges 25, 27 on face 21, for substantially the entire length of panel 12 from edge 23 to edge 15.

Wrap 10 is positioned with inner faces 18, 19 facing the body, with right and left panels 11, 12 under the arms and lateral edges 14, 15 respectively located on either side of the center of the back, so that elastic strips 16, 17 span the hollow region over the spine. The left panel 12 is then brought from left to right, over both breasts, to a point tucked under right panel 11 below the right arm. Right panel 11 is similarly brought from right to left, over both breasts to a point where lateral edge 22 is under the left arm. The panels are secured in overlapping relationship over the breasts by mating the complementary hooks 28, 29 with the respectively corresponding loops 30, 31.

Right panel 11 is sized to extend lengthwise around the chest, from the right edge of the spinal hollow region, under the right arm and over the breasts, to terminate in the left axilla region. Left panel 12 is identically sized to wrap around the chest in the opposite direction. Panels 11, 12 are identically sized in the widthwise direction to extend from a position just above the breasts, to one just below them. Fastening elements 28, 29, 30, 31 are positioned above or below the breasts, so that they will not be pressed against the breasts by the compressive action of the wrap. Darts 34, 35 can be added to run horizontally centrally at the edges 14, 15, if desired, to prevent bunching up of the material between the strips 16, 17 in the vicinity of the spine. The strips 28, 29, 30, 31 provide infinitely variable user-adjustment over the size of the wrap. A selection of five sizes will suitably accommodate bust measurements of 34"-38", 39"-43", 44"-48", 49"-53" and 54"-59", respectively. The width of the wrap may suitably correspondingly be chosen to be $8\frac{1}{2}$"-10". For the 34"-38" bust size, panel length may suitably be $25\frac{1}{2}$" with $1\frac{1}{2}$" separation of edges 14, 15 at strips 16, 17, with strips 16, 17 in their relaxed positions. Elements 28, 29 can be $3\frac{1}{2}$"×$\frac{3}{4}$" strips indented by about $\frac{1}{2}$" from edges 22, 24, 26. Elements 30, 31 can be 19"×$\frac{3}{4}$" strips indented by about $\frac{1}{2}$" from edges 25, 27 and $2\frac{1}{2}$"-$3\frac{1}{2}$" from edges 15, 23.

Figure 5:
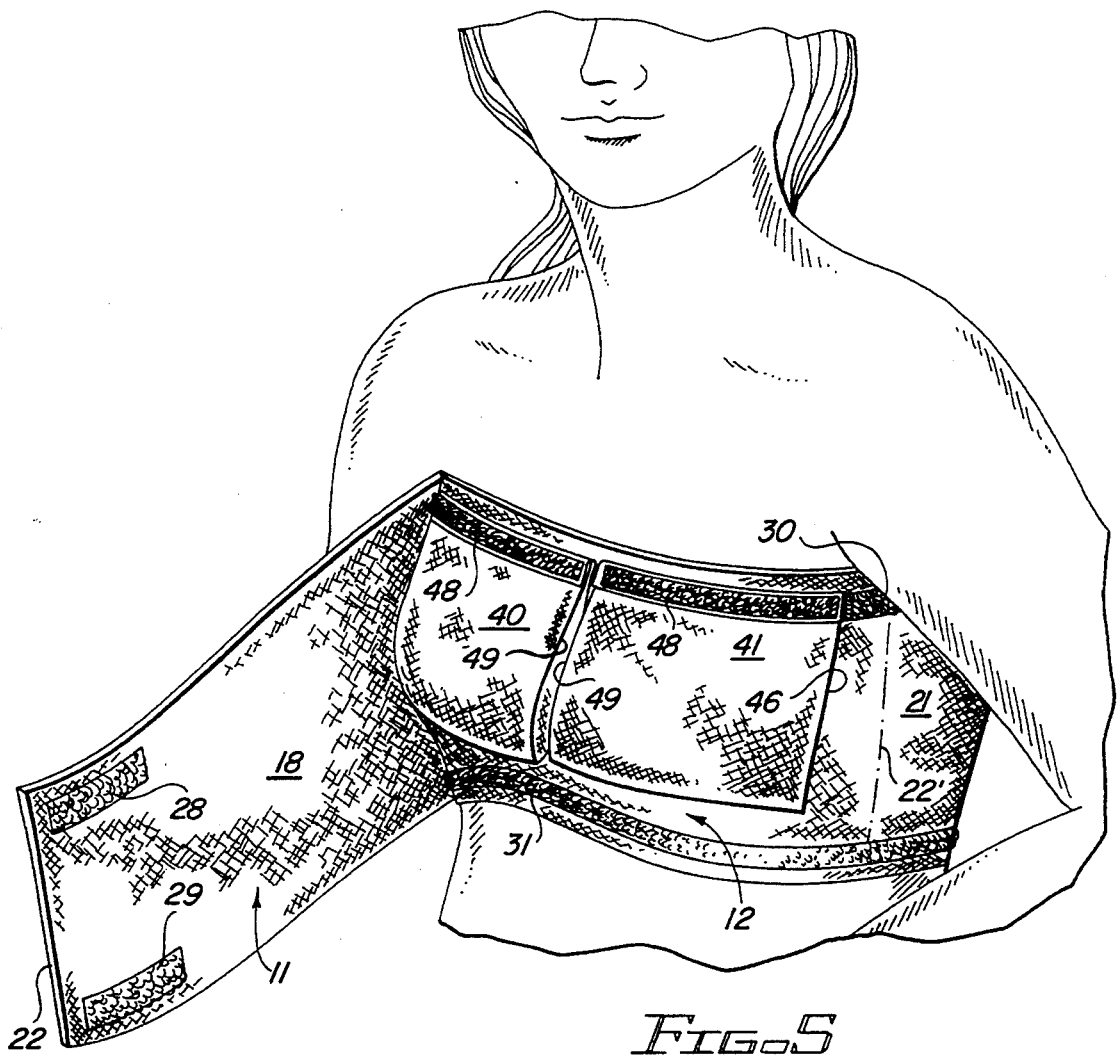
FIG. 5 is a perspective view, as in FIG. 1, of the same wrap showing application of left and right pouches of FIG. 4.

To accommodate the placement of ice packs between the panels 11, 12 of wrap 10, right and left pouches 40, 41 are provided, as shown in FIGS. 4-5. Each pouch comprises front and back rectangular sheets 42, 43 of cotton flannel material sewn along upper and lower longitudinal edges 44, 45 and distal lateral edges 46. A length of hook VELCRO½ fastener 47 is attached longitudinally marginally adjacent edge 44, externally on sheet 43. A length of loop VELCRO½ fastener 48 is attached marginally longitudinally, opposite fastener 47 adjacent edge 44, externally on sheet 42. Sheets 42, 43 are left unjoined along proximal lateral edges 49 to provide a side opening into a pocket 50 formed internally between facing surfaces of sheets 42, 43. Pouches 40, 41 are sized so that a zip-locked bag 51 filled with crushed ice 52; tied, ice-filled surgical glove; disposable cold compress pack; or similar cooling or heating element can be received within the pocket.

As shown in FIG. 5, pouches 40, 41 can be secured between faces 18 and 21 of the overlapping panels 11, 12 by attaching the respective hook elements 47 at desired locations along the loop elements 30. The loop elements 48 of the applied pouches substitute for the underlying elements 30, if needed for attachment of the hook element 28 when the edge 22 of panel 11 is brought into its panel overlapping, dot-dashed position 22', shown in FIG. 5. The open edges 49 of pouches 40, 41 are disposed in facing positions. This arrangement enables ice (or heat) to be applied at any desired position on the breasts. The fasteners 47 can, of course, be affixed to the complementary fasteners 30, 31 to orient the pouches in any desired configuration.

Those skilled in the art to which the invention relates will appreciate that other substitutions and modifications can be made to the described embodiment without departing from the spirit and scope of the invention as described by the claims below.

What is claimed is:

1. A method for compressing the breasts against the chest of a female to alleviate discomfort associated with post-partum engorgement, said method comprising:

providing a wrap including first and second longitudinally extending elongated panels of non-stretchable fabric material having inner and outer face proximal and distal lateral edges, and upper and lower longitudinal edges; at least one strip of longitudinally extending elastic material joining said proximal lateral edges in longitudinal spacing; upper and lower hook-and-loop fastener elements respectively extending longitudinally marginally adjacent said upper and lower longitudinal edges on said second panel outer face: and upper and lower complementary hook-and-loop fastener elements respectively extending longitudinally marginally adjacent said upper and lower longitudinal edges on said first panel inner face;

wrapping said wrap about the chest with said inner faces facing the user's body, said first and second panels under the user's arms, and said proximal lateral edges respectively located on either side of the user's back so that said strip spans the user's spine; said wrapping step comprising:

bringing said second panel longitudinally in a direction about the chest, from said first panel proximal lateral edge located adjacent the spine, under one arm and over both breasts, to terminate with said second panel distal lateral edge located beyond the breasts proximate an axilla region of the other arm;

bringing said first panel longitudinally in an opposite direction about the chest, from said first panel proximal lateral edge located adjacent the spine, under the other arm and in superposed relationship with said second panel over both breasts, to terminate with said first panel distal lateral edge located beyond the breasts proximate a corresponding axilla region of the one arm;

positioning said first and second panels to extend laterally from said upper longitudinal edges located above the breasts to said lower longitudinal edges located below the breasts; and securing said panels in overlapping relationship in compressive action over the breasts, by mating said upper and lower hook-and-loop fastener elements of said first panel respectively with said upper and lower complementary hook-and-loop fastening elements of said second panel; with said fastener elements being positioned respectively above and below the breasts, so that said fastener elements are not pressed against the breasts by said compressive action;

providing at least one pouch having front and back surfaces, and a pocket defined between said front and back surfaces;

inserting cooling material within said pouch; and locating said pouch between said overlapping panels to apply cooling from said cooling material to the breasts.

2. A method as in claim 1, wherein said pouch providing step further comprises providing said pouch with additional complementary hook-and-loop fastener elements located on said back surface; and wherein said pouch locating step further comprises mating said additional complementary hook-and-loop fastener elements to at least one of said second panel upper and lower hook-and-loop fastener elements.

3. A method as in claim 2, wherein said pouch providing step further comprises providing said pouch with additional hook-and-loop fastener elements located on said front surface; and, wherein said pouch locating step further comprises mating said additional hook-and-loop fastener elements to at least one of said first panel upper and lower complementary hook-and-loop elements.

* * * * *